US012773650B2

(12) United States Patent
Singh et al.

(10) Patent No.: US 12,773,650 B2
(45) Date of Patent: Oct. 27, 2026

(54) ENHANCED EXTRACTION OF NATURAL PRODUCTS FROM BIOMASS

(71) Applicant: THE BOARD OF TRUSTEES OF THE UNIVERSITY OF ILLINOIS, Urbana, IL (US)

(72) Inventors: Vijay Singh, Champaign, IL (US); Shivali Banerjee, Urbana, IL (US); Erik Sacks, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 500 days.

(21) Appl. No.: 18/345,309

(22) Filed: Jun. 30, 2023

(65) Prior Publication Data

US 2024/0001258 A1 Jan. 4, 2024

Related U.S. Application Data

(60) Provisional application No. 63/357,917, filed on Jul. 1, 2022.

(51) Int. Cl.
*B01D 11/00* (2006.01)
*B01D 11/02* (2006.01)
(Continued)

(52) U.S. Cl.
CPC ........ *B01D 11/0288* (2013.01); *C12N 9/2437* (2013.01); *C13K 1/02* (2013.01); *B01D 2257/70* (2013.01); *C12Y 302/01004* (2013.01)

(58) Field of Classification Search
CPC ............ B01D 11/0288; B01D 2257/70; B01D 11/0203; B01D 11/028; C12N 9/2437; C13K 1/02; C12Y 302/01004
(Continued)

(56) References Cited

U.S. PATENT DOCUMENTS 7,279,189 B2 * 10/2007 Lauro ........................ A23L 5/43 426/540
2008/0313822 A1 * 12/2008 Bertoldo de Barros ..................... C09B 61/00 8/438

(Continued)

FOREIGN PATENT DOCUMENTS

CN 111187245 A 5/2020
WO 2011047046 A1 4/2011

(Continued)

OTHER PUBLICATIONS

Banerjee et al., "Valorization of Miscanthus x giganteus for sustainable recovery of anthocyanins and enhanced production of sugars", Journal of Cleaner Production 369, Article 133508, 7pgs, Aug. 2022.

(Continued)

*Primary Examiner* — Eisa B Elhilo
(74) *Attorney, Agent, or Firm* — Haukaas Fortius PLLC; Michael Haukaas

(57) ABSTRACT

*Miscanthus* x *giganteus* is a widely recognized bioenergy crop that finds potential applications in a biorefinery for the production of a wide range of biofuels and biochemicals. This disclosure focuses upon the quantification of the total anthocyanin concentration in *miscanthus*. Hydrothermal pretreatment was studied for recovering anthocyanins in the pretreatment liquor. The optimized pretreatment conditions (170° C., 10 min) led to a recovery of 94.3±1.5% w/w of the total anthocyanin concentration and also improved the enzymatic digestibility of the biomass, allowing recovery of 70.6±0.5% w/w of glucose at the end of 72 h of enzymatic saccharification. The sugar monomers obtained after the enzymatic hydrolysis of the pretreated biomass could be
(Continued)

used for the production of biofuels or biochemicals in an integrated biorefinery.

5 Claims, 5 Drawing Sheets

(51) Int. Cl.
*C12N 9/42* (2006.01)
*C13K 1/02* (2006.01)
(58) Field of Classification Search
USPC .............................................................. 8/636
See application file for complete search history.

(56) References Cited

U.S. PATENT DOCUMENTS

| | | | |
|---|---|---|---|
| 2017/0159091 A1 | 6/2017 | Yuan et al. | |
| 2020/0352980 A1* | 11/2020 | Mahowald | A61K 45/06 |
| 2021/0137964 A1* | 5/2021 | von Maltzahn | A61P 1/10 |
| 2021/0161942 A1* | 6/2021 | von Maltzahn | A61K 9/0053 |

FOREIGN PATENT DOCUMENTS

| | | | |
|---|---|---|---|
| WO | 2015050683 A1 | 4/2015 | |
| WO | WO 2017015539 A1 * | 1/2017 | C09B 61/00 |

OTHER PUBLICATIONS

Cheynier, Veronique., "Polyphenols in foods are more complex than often thought", Am J Clin Nutr., 81(suppl):223S-9S, Jan. 2005.
Kurambhatti et al., "Technical and economic feasibility of an integrated ethanol and anthocyanin coproduction process using purple corn stover", Biofuels, Bioprod. Bioref. 15:719-735, Mar. 2021.
Mai, C., "Concentration of Hot Water Extracts of Anthocyanins obtained from Muscadine Grape Pomace using Membrane-Osmotic Distillation", Food Science Undergraduate Honors Theses Retrieved from https://scholarworks.uark.edu/fdscuht/9, 20pgs, May 2019.
Maitra et al., "Balancing sugar recovery and inhibitor generation during energycane processing: Coupling cryogenic grinding with hydrothermal pretreatment at low temperatures", Bioresour Technol. 321:124424, Feb. 2021.
Singh et al., "Hydrothermal pretreatment for valorization of genetically engineered bioenergy crop for lipid and cellulosic sugar recovery", Bioresource Tech. 341, 125817, Dec. 2021.
Singh et al., "Integrated Biorefinery for Valorization of Engineered Bioenergy Crops—A Review", vol. 17, Issue 5, Oct. 2021.
Sridhar et al., "Techniques and modeling of polyphenol extraction from food: a review", Environ Chem Lett 19(4):3409-3443, Mar. 2021.
Tan et al., "Extraction and purification of anthocyanins: A review", Journal of Agriculture and Food Research, vol. 8, 100306, Jun. 2022.

* cited by examiner

ENHANCED EXTRACTION OF NATURAL PRODUCTS FROM BIOMASS

RELATED APPLICATIONS

This application claims priority under 35 U.S.C. § 119(e) to U.S. Provisional Patent Application No. 63/357,917, filed Jul. 1, 2022, which is incorporated herein by reference.

GOVERNMENT SUPPORT

This invention was made with government support under Grant No. DE-SC0018420 awarded by the Department of Energy. The government has certain rights in the invention.

BACKGROUND OF THE INVENTION

Synthetic colorants are among the harmful chemicals that are known to cause serious environmental pollution and lead to a disturbed ecological balance. For these reasons, the use of natural colorants is attracting significant interest among the dyeing industries. The global market of natural colorants is growing fast and is anticipated to generate revenues of approximately USD 5 billion by 2024, growing at a compound annual growth rate (CAGR) of around 11% during 2018-2024. Anthocyanins are among the most common plant-derived colorants present in berries, grapes, purple tubers, purple leafy vegetables, and purple grains. However, these have a well-established market in the food sector and cannot be diverted completely for the recovery of industrial pigments such as anthocyanins. Hence, there is a need to explore alternative sources of anthocyanins. The presence of industrially relevant pigments in bioenergy crops such as *miscanthus*, sorghum, and sugarcane has been previously reported. The red pigment, present in the leaf sheaths of sorghum, is rich in 3-deoxyanthocyanins which are known for their stability to heat treatments and pH changes, making them a valuable source of natural colorants for industrial applications. In the case of sugarcane and *miscanthus*, the pigment is mostly concentrated in the stem of the plant. The utilization of these bioenergy crops for the extraction of anthocyanin-based colorants is uncommon. These crops hold enormous potential as a resource for extracting pigments as a co-product. Among the different bioenergy crops, *M.* x *giganteus* is a perennial grass that has gained attention as a potential bioenergy crop due to its non-invasive nature, high biomass yields and low input requirements.

In previous studies, anthocyanins have been recovered using polar organic solvent. On an industrial scale, the application of organic solvents for recovering anthocyanins is not sustainable and might have an environmental impact. To meet the large-scale demand for natural colors for industrial applications, the extraction process should be economically viable and environmentally sustainable, along with an abundant supply of feedstock. In this study, a hydrothermal pretreatment step was assessed as a process for recovering anthocyanins from purple-stemmed *miscanthus*. Hydrothermal pretreatment has advantages over other chemical pretreatments/extraction methods because compressed hot water is used as the only solvent, thereby decreasing the operating costs as well as the effects on the environment. Different combinations of temperature and time were studied to obtain the maximum recovery of anthocyanins. Pretreatment also reduces the recalcitrant nature of lignocellulosic biomass and leads to enhanced enzymatic digestibility. The enzymatic digestibility of the pretreated residue was also evaluated for its conversion into biofuels or biochemicals in an integrated biorefinery. To the best of our knowledge, *miscanthus* has never been explored as a source of anthocyanins. Also, the chemical-free hydrothermal method for the extraction of anthocyanins from purple stemmed *miscanthus* has never been reported.

Accordingly, there is a need for a safe, economical, and chemical-free hydrothermal method for the extraction of anthocyanins.

SUMMARY

This disclosure provides a chemical-free hydrothermal process for recovering anthocyanins from purple-stemmed *miscanthus*. Hydrothermal pretreatment has advantages over other chemical pretreatments/extraction methods because compressed hot water is used as the only solvent, thereby decreasing the operating costs as well as the effects on the environment. Pretreatment also reduces the recalcitrant nature of lignocellulosic biomass and leads to enhanced enzymatic digestibility.

To date there have been no reports of a chemical-free hydrothermal method for the extraction of anthocyanins from purple stemmed *miscanthus*. Therefore, different combinations of temperature and time were studied to obtain the maximum recovery of anthocyanins. The enzymatic digestibility of the pretreated residue was also evaluated for its conversion into biofuels or biochemicals in an integrated biorefinery.

Accordingly, this disclosure provides a hydrothermal method for extracting anthocyanin from a crop comprising:

a) heating a mixture of a crop, such as a lignocellulosic crop, in water at a suitable temperature, pressure, and an amount of time heating at the suitable temperature and pressure, wherein at least 80 wt. % of the total amount of anthocyanin in the crop is extracted into the water of the heated mixture to form a water extract and an extracted crop; and b) cooling the heated mixture to below about 50° C.; wherein the water extract comprises the anthocyanin.

Also, this disclosure provides a method such as the method above that further comprises:

c) separating the extracted crop from the water by filtering, centrifuging, or a combination thereof; and d) hydrolyzing the extracted crop with an enzyme; wherein glucose is thereby recovered from the crop.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
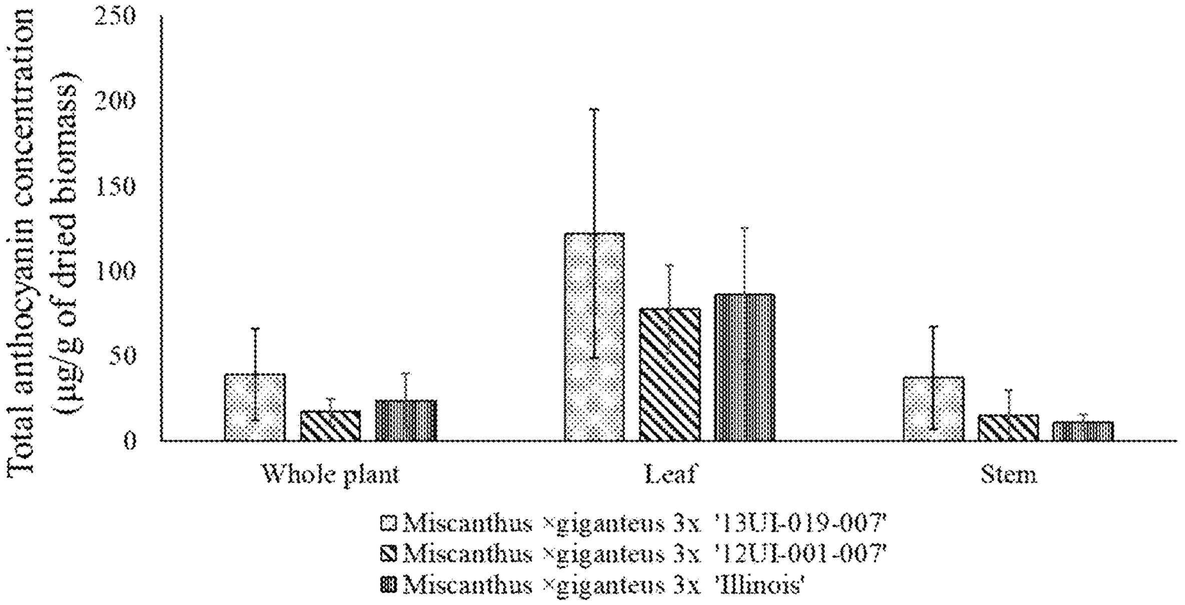
FIG. 1. Total anthocyanin concentration in three different triploid *Miscanthus* x *giganteus* genotypes (a) whole shoot, (b) leaves and (c) stem.

The increased awareness for eco-friendliness and sustainability has shifted the interest of stakeholders from synthetic colors to natural plant-based pigments. In this study, purple stemmed *Miscanthus* x *giganteus* was evaluated as a source of anthocyanins. Hydrothermal pretreatment was studied as a green, chemical-free process for recovering maximum anthocyanins in the pretreatment liquor. The highest recovery of 94.3 ±1.5% w/w of the total anthocyanin concentration was obtained for a temperature and time combination of 170° C. and 10 min. The pretreatment also improved the enzymatic digestibility of the biomass and led to a 2.1-fold increase in the overall recovery of glucose (70.6±0.5% w/w) at the end of 72 h. The sugar monomers obtained after the enzymatic hydrolysis of the pretreated biomass could be used for the production of biofuels or biochemicals in an integrated biorefinery based on purple-stemmed *miscanthus*. Overall, this study demonstrates that the clean pretreatment method developed could lead to an additional product stream (rich in anthocyanins) along with its effect in reducing the recalcitrance of *miscanthus* biomass.

Additional information and data supporting the invention can be found in the following publication by the inventors and their coauthors: *Journal of Cleaner Production* 369 (2022) 133508, which is incorporated herein by reference in its entirety.

Definitions.

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability, necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

The recitation of a), b), c), . . . or i), ii), iii), or the like in a list of components or steps do not confer any particular order unless explicitly stated.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The term "lignocellulosic crop" refers to plant biomass (or dry matter), which can be any biomass rich in cellulose, hemicelluloses, and lignin.

The term "extracted crop" refers to the solid residue after the crop or lignocellulosic crop has been hydrothermally pretreated to improve enzymatic digestibility of the solid residue that is cellulose-enriched.

Embodiments of the Technology.

This disclosure provides a hydrothermal method for extracting anthocyanin from a crop comprising:

a) heating a mixture of a crop in water at a suitable (maximum) temperature, pressure, and an amount of time heating at the suitable temperature and pressure, wherein at least 50 wt. % of the total amount of anthocyanin in the crop is extracted into the water of the heated mixture to form a water extract and an extracted crop; and b) rapidly cooling the heated mixture to below about 50° C.; wherein the water extract comprises the anthocyanin.

In various embodiments, the crop is a lignocellulosic crop. In other various embodiments, the crop is *miscanthus*, sorghum, sugarcane, or poaceae. In certain embodiments, the crop is not a vegetable or fruit. In various embodiments, the crop has been dried and shredded.

In some embodiments, the temperature is about 25° C. to about 250° C. In some other embodiments, the temperature is about 160° C. to about 190° C. In yet other embodiments, the temperature is about 170° C. to about 180° C. In some other embodiments, the temperature is about 100° C., about 110° C., about 130° C., about 140° C., about 145° C., about 150 ° C., about 155° C., about 160° C., about 165° C., about 170° C., about 175° C., about 180° C., about 185° C., about 190° C., about 200° C., or about 225° C.

In some embodiments, the cooling of the heated mixture is to below or above about 40° C., about 30° C., about 20° C., about 10° C., about 0° C., or about ambient temperature.

In some embodiments, the pressure is greater than 1 atmosphere (atm). In some embodiments, the pressure is about 6 atmospheres to about 12 atmospheres. In some embodiments, the pressure is about 2 atm, about 3 atm, about 4 atm, about 5 atm, about 6 atm, about 7 atm, about 8 atm, about 9 atm, about 10 atm, about 11 atm, about 12 atm, about 13 atm, about 14 atm, or about 15 atm.

In some embodiments, the amount of time heating at the suitable temperature and pressure is about 5 minutes to about 15 minutes, wherein the suitable temperature is a maximum temperature. In some embodiments, the amount of time heating at the suitable temperature and pressure is about 6.5 minutes to about 12.5 minutes. In some embodiments, the amount of time heating at the maximum temperature is about 2 minutes (min), about 3 min, about 4 min, about 5 min, about 6 min, about 7 min, about 8 min, about 9 min, about 10 min, about 11 min, about 12 min, about 13 min, about 14 min, about 15 min, about 16 min, about 17 min, about 18 min, about 19 min, about 20 min, about 25 min, or about 30 min.

In some embodiments, the cooling is at a rate of about 2° C/minute to about 20° C./minute. In some embodiments, the cooling is at a rate of about 5° C./minute to about 10° C./minute. In some embodiments, the cooling is at a rate of about 4° C./minute (° /min), about 6° C./min, about 8° C./min, about 10° C./min, about 12° C./min, about 14° C./min, about 16° C./min, about 18° C./min, about 20° C./min, about 22° C./min, about 24° C./min, about 26° C./min, about 28° C./min, or about 30° C./min.

In various embodiments, the mixture does not contain an organic solvent. In various embodiments, at least 90 wt. % of the total amount of anthocyanin in the crop is extracted by the water. In various embodiments, the amount of anthocyanin in the crop that is extracted by the water is about 60 wt. %, about 70 wt. %, about 80 wt. %, about 85 wt. %, about 90 wt. %, about 95 wt. %, about 96 wt. %, about 97 wt. %, about 98 wt. %, or about 99 wt. %.

In some embodiments, the water extract comprises 38.7±26.9 mg/g anthocyanin, 1.85±0.07 g/100 g glucose, 1.51±0.04 g/100 g xylose, 0.76±0.04 g/100 g arabinose, 0.17±0.01 g/100 g lactic acid, 0.18±0.00 g/100 g acetic acid, 0 g/100 g furfural, and 0 g/100 g 5-hydroxymethylfurfural, based on a dry weight of an above-ground whole shoot of the crop, wherein the crop is *Miscanthus* x *giganteus*.

In some embodiments, the method further comprises separating the water extract from the extracted crop that are in the cooled mixture by filtering, centrifuging, or a combination thereof. In some embodiments, the method further comprises enzymatically hydrolyzing the extracted crop. In some embodiments, the crop is enzymatically hydrolyzed by cellulase and/or hemicellulase.

In a preferred embodiment, the method for extracting anthocyanin from a crop comprises:

a) heating a mixture of a crop and water at a temperature of about 160° C. to about 190° C. under pressure for a heating time of about 5 minutes to about 15 minutes at the temperature to form a heated mixture; and b) cooling the heated mixture at a cooling rate of about 2° C./minute to about 20° C./minute until the heated mixture is at a temperature below about 50° C.; wherein a water extract comprising dissolved anthocyanin is thereby formed.

Additionally, this disclosure provides a method for recovering glucose from a crop comprising:

a) heating a mixture of a crop in water to a temperature of about 160° C. to about 190° C. under pressure for a heating time of about 5 minutes to about 15 minutes at the temperature to form a heated mixture;

b) cooling the heated mixture at a cooling rate of about 2° C./minute to about 20° C./minute until the heated mixture is at a temperature below about 50° C., therby forming an extracted crop;

c) separating the extracted crop from the water by filtering, centrifuging, or a combination thereof; and d) hydrolyzing the extracted crop with an enzyme; wherein glucose is thereby recovered from the crop.

In some embodiments, the enzyme is cellulase, hemicellulase, or a combination thereof. In some embodiments, the extracted crop is hydrolyzed by the enzyme for at least 12 hours. In some other embodiments, the extracted crop is hydrolyzed by the enzyme for about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours, or about 96 hours.

In various embodiments, the crop is *miscanthus*, sorghum, sugarcane, or poaceae. In some embodiments, the heating time is about 6 minutes to about 12 minutes, and the cooling rate is about 5° C./minute to about 10° C./minute. In certain embodiments, the crop is *miscanthus*, the temperature is about 170° C., and the time is about 10 minutes.

This disclosure also provides a composition comprising about 15-65 mg/g anthocyanin, about 1.6-2.1 g/100 g glucose, about 1.5-1.9 g/100 g xylose, about 0.3-0.8 g/100 g arabinose, about 0.03-0.2 g/100 g lactic acid, about 0.1-0.3 g/100 g acetic acid, about 0-0.03 g/100 g furfural, and 0 g/100 g 5-hydroxymethylfurfural.

In some embodiments, the composition comprises 38.7±26.9 mg/g anthocyanin, 1.85±0.07 g/100 g glucose, 1.51±0.04 g/100 g xylose, 0.76±0.04 g/100 g arabinose, 0.17 ±0.01 g/100 g lactic acid, 0.18 ±0.00 g/100 g acetic acid, 0 g/100 g furfural, and 0 g/100 g 5-hydroxymethylfurfural.

Results and Discussion.

Composition of *miscanthus* samples. Table 1 lists the composition (total extractives, carbohydrates, lignin, and ash) of three different *M.* x *giganteus* genotypes. The carbohydrate content of *miscanthus* samples ranged from 55.6 to 67.2% (w/w dry basis (d.b.)). The total extractives content in *miscanthus* was around 11.3-14.0% (w/w d.b.), which was high relative to the 0.3-2.2% reported previously (Brosse et al., Biofuels, Bioproducts and Biorefining, 6(5), 580-598, 2012). Similarly, 5.57% and 1.02% of extractives were obtained from *miscanthus* by the Soxhlet method with ethanol/toluene (1:2) and dichloromethane, respectively (Wang et al., Energies, 11(1), 2018). The high content of total extractives in *miscanthus* in the present study could be attributed to the sum of hexane, ethanol and water-based extractives obtained by the Soxhlet method. The previously reported studies had not considered the contribution of water-based extractives to the total extractives. The water-based extractives obtained by the Soxhlet method consists of sugars.

TABLE 1

Chemical composition of shoots for three different triploid *Miscanthus* x *giganteus* genotypes.

| Entry | Extractives (% w/w) | Total glucan (% w/w) | Total xylan (% w/w) | Total ash (% w/w) | AIL (% w/w) (excluding Ash) | ASL in total biomass (% w/w) |
|---|---|---|---|---|---|---|
| *M.* x *giganteus* 3x '13UI-019-007' | 11.3 ± 1.9 | 41.4 ± 1.8 | 21.2 ± 2.6 | 2.8 ± 0.4 | 19.9 ± 1.0 | 2.0 ± 0.1 |
| *M.* x *giganteus* 3x '12UI-001-007' | 13.7 ± 1.0 | 39.1 ± 2.9 | 23.5 ± 2.9 | 3.0 ± 0.5 | 21.3 ± 1.5 | 2.0 ± 0.1 |
| *M.* x *giganteus* 3x 'Illinois' | 14.0 ± 2.0 | 38.3 ± 0.8 | 20.6 ± 2.2 | 3.0 ± 0.5 | 23.1 ± 0.2 | 2.1 ± 0.1 |

Values represent average ± standard deviation;
AIL: Acid insoluble lignin;
ASL: Acid soluble lignin.

Total anthocyanin concentration in *miscanthus* biomass. *M.* x *giganteus* 3x '13UI-019-007' had the highest anthocyanin concentration (38.7±26.9 μg/g of dried biomass) of the three genotypes tested (FIG. 1). *Miscanthus* whole shoots had a lower anthocyanin concentration in comparison to other anthocyanin-rich crops such as purple corn (7.5 mg/g dry matter), blueberries (7.2±0.5 mg/g dry matter), black carrot (0.04-17.4 mg/g dry matter), red cabbage (11.1-17.8 mg/g dry matter) and black grape pomace (1.9 mg/g dry matter). However, the anthocyanin concentration of the three *miscanthus* genotypes in this study was comparable to that of other crop biomass such as sugarcane tips, stem, and peel (2.5-82 μg/g of dried biomass); sugarcane rind (110.6-132.0 μg/g of dry weight) and rice straw (0.51-0.63 mg/g of dried biomass). The higher productivity of bioenergy grass crops might lead to an increase in the total quantity of anthocyanins produced per hectare. For example, 0.9-2.7 kg of anthocyanins per hectare could be obtained from the current *M.* x *giganteus* genotypes, which is comparable to 1.6-3.2 kg of anthocyanins from grape pomace per hectare (calculations not shown). Similarly, the bioenergy crop *Sorghum bicolor* (leaf sheath) could yield 12.1 kg of anthocyanin per hectare, which is more than the 7.6 kg per hectare yield from blueberries (calculations not shown). The concentration of anthocyanins in these crops could be increased by inducing stress conditions (such as drought, high salinity, excess light, and low temperature) during their cultivation or by genetic modification.

The total anthocyanin concentration was found to be higher in *miscanthus* leaves (per gram basis) compared to the stem. Since the proportion of leaves in whole *miscanthus* shoots is less than that of the stem, the major contribution of anthocyanin concentration in the whole shoot comes from the stem. Because selection '13UI-019-007' had the highest anthocyanin concentration of the three *M.* x *giganteus* genotypes we tested, it was chosen for further experiments on the recovery of anthocyanins via hydrothermal pretreatment.

Hydrothermal pretreatment for recovery of anthocyanins. In hydrothermal pretreatment, hydronium ions catalyze the degradation of hemicellulose. In the present case, these hydronium ions might have provided an acidic environment to the liquor that stabilized the anthocyanins.

However, at higher temperatures with prolonged pretreatment time, the anthocyanins underwent thermal degradation, resulting in decreased recovery. Hence optimized conditions were obtained to recover maximum yields of anthocyanins from *miscanthus*. Previous studies have reported the efficiency of acidified water, pressurized hot water, and subcritical water in extracting anthocyanins from fruits and vegetables such as blueberries, raspberries, red chicory and red onion. However, the composition of fruits and vegetables differs from bioenergy crops, the latter being more recalcitrant towards mild extraction conditions.

TABLE 2

Summary of average percent recovery of anthocyanins after hydrothermal pretreatment of *M.* × *giganteus* 3x '13UI-019-007' shoots.

| Temperature (° C.) | Time (min) | Severity factor | Recovery of anthocyanins (% w/w) |
|---|---|---|---|
| 130 | 5 | 1.582 | 19.4 ± 1.8$^{e}$ |
| 130 | 10 | 1.883 | 25.5 ± 1.7$^{e}$ |
| 130 | 15 | 2.059 | 28.4 ± 1.8$^{d,\ e}$ |
| 150 | 5 | 2.171 | 24.4 ± 3.1$^{e}$ |
| 150 | 10 | 2.472 | 36.8 ± 3.1$^{c,\ d}$ |
| 150 | 15 | 2.648 | 39.8 ± 8.1$^{c}$ |
| 170 | 5 | 2.760 | 78.8 ± 3.5$^{b}$ |
| 170 | 10 | 3.061 | 94.3 ± 1.5$^{a}$ |
| 170 | 15 | 3.237 | 36.7 ± 6.1$^{c,\ d}$ |
| 190 | 5 | 3.349 | 77.2 ± 4.4$^{b}$ |
| 190 | 10 | 3.650 | n.d. |
| 190 | 15 | 3.826 | n.d. |

Values represent average ± standard deviation;
values sharing the same alphabet are not significantly different ($p < 0.05$);
n.d. means not detected.

Figure 2:
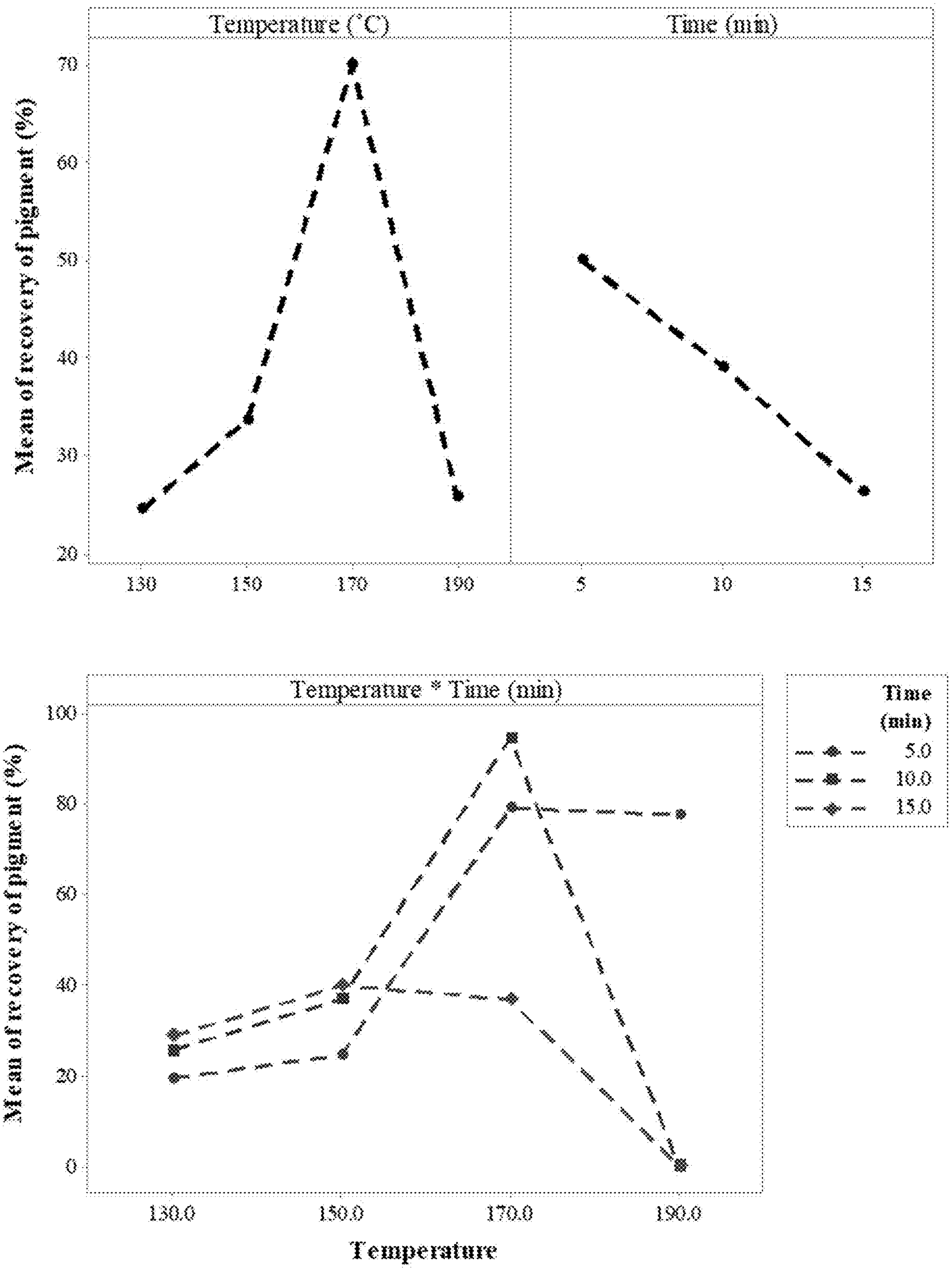
FIG. 2. Main effects and interaction plots for the effect of extraction temperature and time on % recovery of anthocyanin from *M.* x *giganteus* 3x '13UI-019-007' shoots.
Figure 3:
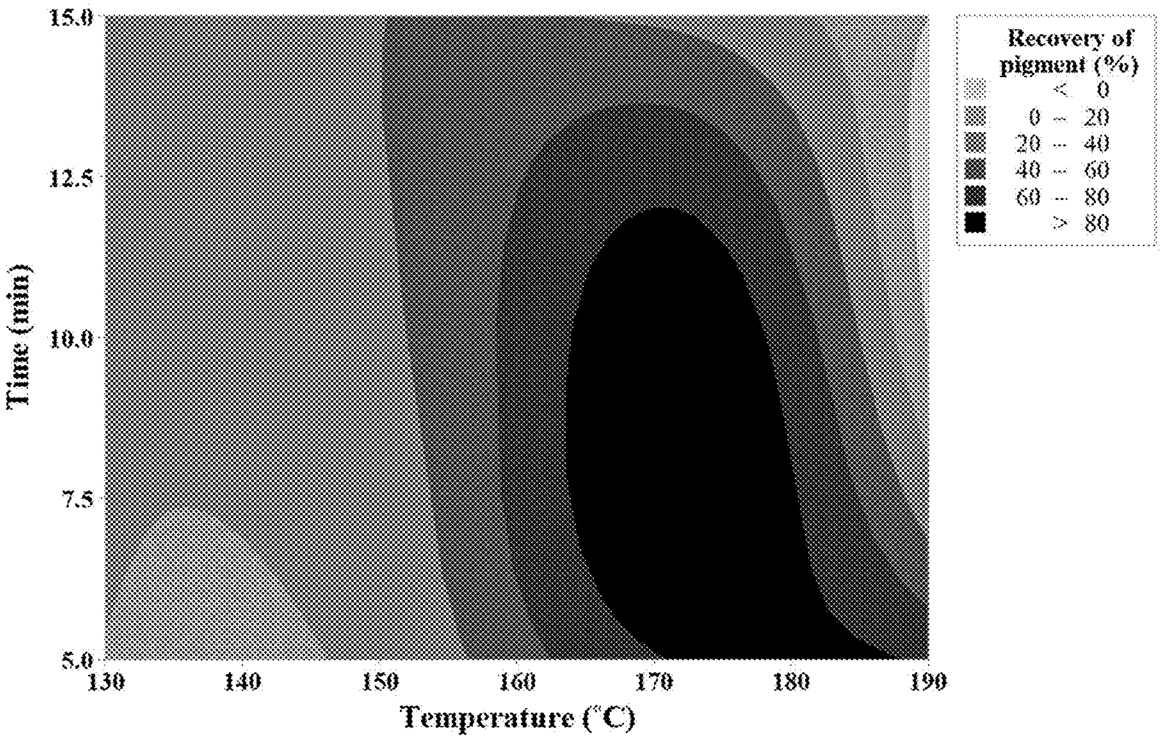
FIG. 3. Contour plot showing the relative recovery of anthocyanins *M.* x *giganteus* 3x '13UI-019-007' shoots at different temperatures (° C.) and time (min).

In the present study, the maximum recovery of 94.3±1.5% (w/w) of anthocyanin was obtained after the hydrothermal pretreatment of *M.* x *giganteus* at 170° C. for 10 min (Table 2). The statistical model for recovery of pigment contains two main effect terms (temperature (° C.) and time (min)) and one interaction term. The individual main effect terms as well as the interaction term of the model were found to be significant ($p<0.05$) (Table 3). The R2 and adjusted R2 for this model were 98.9% and 98.4%, respectively indicating a good fit for the model. The main effect and interaction plots (FIG. 2) represent that both, temperature (° C.) and time (min) of hydrothermal pretreatment influence the recovery of anthocyanins from *M.* x *giganteus* biomass. For lower pretreatment temperatures (130 and 150 ° C.), the maximum 15 recovery of pigments was observed at a longer holding time (15 min), which could be attributed to the time taken for the effective release of pigments from the biomass structure. However, prolonged holding time (15 min) at the optimized temperature (170° C.) or above (190° C.) led to a decrease in the recovery of pigments, which is mainly due to the degradation of these pigments. The contour plot (FIG. 3) also depicts that the pretreatment temperature and time both influence the recovery of pigments from *miscanthus*. More than 80% (w/w) of pigments could be recovered at the pretreatment temperature range of 170-180° C. for 5-12 min. Increasing the temperature above 180° C. led to a decrease in the percent recovery of pigments. Lower pretreatment duration (5 min) at high temperatures (190° C.) could yield more than 60% (w/w) recovery of pigments.

TABLE 3

Analysis of variance (ANOVA) for effects of pretreatment temperature (° C.) and time (min) on the % recovery of anthocyanins from *M.* × *giganteus* 3x '13UI-019-007' shoots.

| Source | DF | Adj SS | Adj MS | F | P |
|---|---|---|---|---|---|
| Temperature (° C.) | 3 | 12337.9 | 4112.6 | 299.6 | <0.001 |
| Time (min) | 2 | 3389.5 | 1694.7 | 123.5 | <0.001 |
| Temperature (° C.) * Time (min) | 6 | 14470.0 | 2411.7 | 175.7 | <0.001 |
| Error | 24 | 329.4 | 13.7 | | |
| Total | 35 | 30526.9 | | | |

$R^2$ = 98.9%;
Adjusted $R^2$ = 98.4%;
Predicted $R^2$ = 97.6%

High temperatures are known to degrade anthocyanins, but the combined effect of temperature and time controls the stability of anthocyanins. Studies have reported the application of subcritical water (i. e., remains in a liquid state under high pressure and temperature range of 100-374° C.) for a short duration of time for enhanced recovery of bioactive compounds. In a recent study, the optimal conditions for the subcritical water extraction of anthocyanins from blueberries led to a recovery of 0.47±0.03 mg/g of fresh weight at 130° C. for 3 min, while for chokeberry, the optimal conditions at 190° C. for 1 min led to an anthocyanin recovery of 0.66±mg/g of fresh weight. Similarly, subcritical water extraction of anthocyanins from raspberry under optimal conditions (at 130° C. for 90 min at an extraction pressure of 7 MPa) led to the maximum recovery of 98.9±0.3 mg/100 g). The optimum temperature and time for maximum recovery of anthocyanins via subcritical water extraction vary with the kind of feedstock.

Composition of pretreatment liquor. The pretreatment liquor mainly comprises anthocyanins, sugars, organic acids, and degradation products (furfurals and 5-HMF) as shown in Table 4. Glucose (1.3-4.9 g/100 g of dried biomass), xylose (1.5-5.5 g/100 g of dried biomass), and arabinose (0.05-0.8 g/100 g of dried biomass) are the major sugar monomers present in the pretreatment liquor at different severity levels. An increase in the severity of the pretreatment resulted in decreased concentration of sugar monomers (glucose and xylose), which could be attributed to their conversion into 5-HMF and furfural, respectively. Higher severity (e.g. 3.8) led to an increased concentration of sugar monomers in the pretreatment liquor along with the enhanced production of furfurals and 5-HMF. The increased concentration of sugar monomers with the increase in severity could be attributed to the autohydrolysis of glucan and xylan under high temperatures and longer reaction time. The pretreatment liquor obtained under optimal conditions for the maximum recovery of anthocyanins (170° C., 10 min) does not contain degradation products such as furfural and 5-HMF. The concentration of these degradation products increased upon prolonged heating at pretreatment temperatures beyond 170° C. A similar trend has been reported in the literature for the hydrothermal pretreatment of energy cane bagasse, where the total concentration of degradation products (such as furfurals and 5-HMF) increased exponentially beyond 170° C.

TABLE 4

Composition of pretreatment liquor (expressed as g per 100 g of biomass on dry basis) derived from hydrothermal pretreatment of *M.* x *giganteus* 3x '13UI-019-007' shoots.

| Temp. (° C.) | Time (min) | Severity | Glucose (g/100 g) | Xylose (g/100 g) | Arabinose (g/100 g) | Lactic acid (g/100 g) | Acetic acid (g/10 g) | Furfural (g/100 g) | 5-HMF (g/100 g) |
|---|---|---|---|---|---|---|---|---|---|
| 130 | 5 | 1.582 | 2.67 ± 0.03 | 1.80 ± 0.00 | 0.05 ± 0.02 | n.d. | 0.03 ± 0.00 | n.d. | n.d. |
| | 10 | 1.883 | 2.75 ± 0.06 | 1.86 ± 0.05 | 0.11 ± 0.03 | 0.03 ± 0.00 | 0.03 ± 0.00 | n.d. | n.d. |
| | 15 | 2.059 | 2.76 ± 0.09 | 1.74 ± 0.05 | 0.05 ± 0.03 | n.d. | 0.06 ± 0.00 | n.d. | n.d. |
| 150 | 5 | 2.171 | 2.97 ± 0.21 | 1.94 ± 0.12 | 0.26 ± 0.02 | 0.03 ± 0.00 | 0.06 ± 0.00 | n.d. | n.d. |
| | 10 | 2.472 | 2.14 ± 0.15 | 1.70 ± 0.09 | 0.53 ± 0.10 | 0.12 ± 0.03 | 0.11 ± 0.01 | n.d. | n.d. |
| | 15 | 2.648 | 2.10 ± 0.03 | 1.93 ± 0.03 | 0.31 ± 0.01 | 0.03 ± 0.0 | 0.13 ± 0.01 | n.d. | n.d. |
| 170 | 5 | 2.760 | 2.02 ± 0.40 | 1.62 ± 0.08 | 0.48 ± 0.08 | 0.12 ± 0.04 | 0.11 ± 0.02 | n.d. | n.d. |
| | 10 | 3.061 | 1.85 ± 0.07 | 1.51 ± 0.04 | 0.76 ± 0.04 | 0.17 ± 0.01 | 0.18 ± 0.00 | n.d. | n.d. |
| | 15 | 3.237 | 1.92 ± 0.21 | 1.53 ± 0.05 | 0.35 ± 0.11 | 0.10 ± 0.04 | 0.19 ± 0.07 | 0.02 ± 0.01 | n.d. |
| 190 | 5 | 3.349 | 1.55 ± 0.06 | 1.53 ± 0.03 | 0.66 ± 0.03 | 0.21 ± 0.03 | 0.33 ± 0.03 | 0.03 ± 0.00 | n.d. |
| | 10 | 3.650 | 1.29 ± 0.05 | 1.84 ± 0.11 | 0.69 ± 0.00 | 0.54 ± 0.05 | 1.16 ± 0.07 | 0.24 ± 0.00 | 0.35 ± 0.04 |
| | 15 | 3.826 | 4.86 ± 1.35 | 5.55 ± 0.54 | 0.54 ± 0.00 | 1.52 ± 0.48 | 2.37 ± 0.49 | 1.00 ± 0.43 | 2.1 ± 0.62 |

Values represent average ± standard deviation;
n.d. means not detected.

The degradation of sugars generates furfural and 5-HMF while the acetyl groups present on the hemicellulose backbone generates acetic acid as the degradation product. The acetic acid produced contributes to the acidity of in-situ generated hydronium ions during autohydrolysis and supports the hydrolysis of the polysaccharide backbone. Under different pretreatment severity for *miscanthus*, the concentration of furfural and 5-HMF was in the range of 0.02-1.00 g/100 g of dried biomass and 0.35-2.10 g/100 g of dried biomass, respectively. Similarly, the concentration of acetic acid increased from 0.03 to 2.37 g/100 g of dried biomass upon increasing the severity of pretreatment. An increasing trend in the concentration of lactic acid from 0.1 to 1.5 g/100 g of dried biomass was observed for severity values above 3.2.

Figure 4:
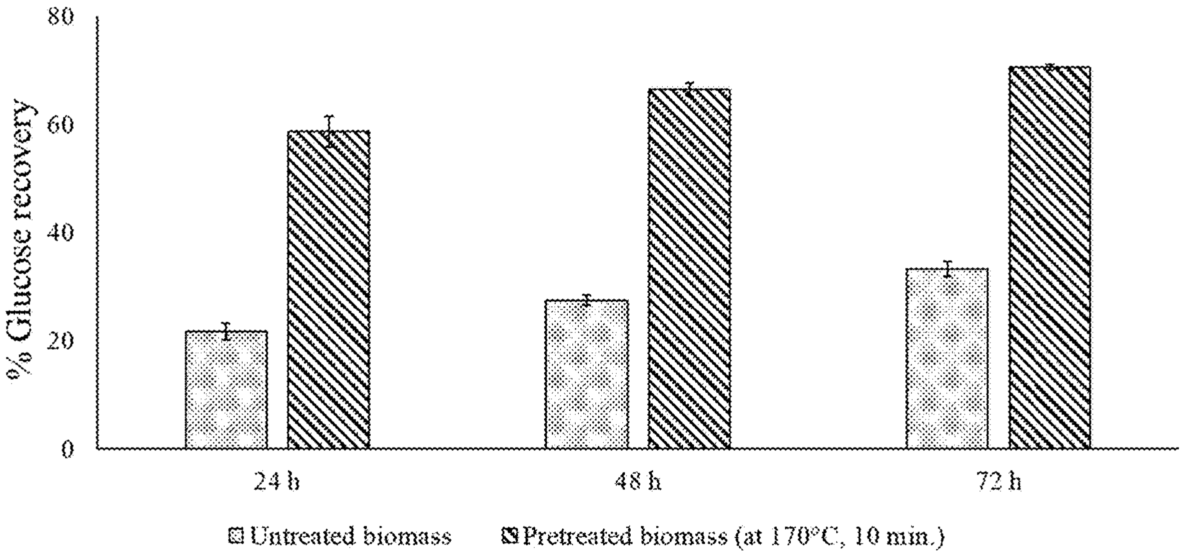
FIG. 4. Recovery of glucose from untreated and pretreated *M* x *giganteus* 3x '13UI-019-007' shoots after (a) 24 h, (b) 48 h and (c) 72 h of enzymatic hydrolysis.

Enzymatic hydrolysis. Hydrothermal pretreatment is known for its efficacy in increasing the enzymatic digestibility of cellulose-enriched residue. Enzymatic hydrolysis is commonly used to valorize the pretreated residue into sugar monomers. The biomass pretreated at 170° C. for 10 min showed the highest anthocyanin concentration in the liquor and the residue was used for enzymatic hydrolysis. The amount of glucose released over time upon enzymatic hydrolysis is as shown in FIG. 4. The % recovery of glucose upon enzymatic saccharification increased from 58.6 ±2.8% at 24 h to 70.6±0.5% after 72 h. However, for untreated *miscanthus* biomass, only 33.3±1.4% of glucose was released after 72 h. The glucose recovery increased with time and the pretreatment led to a 2.1- fold increase in the overall recovery of glucose from the pretreated biomass at the end of 72 h. The improved enzymatic digestibility of biomass upon hydrothermal pretreatment could be attributed to the disruption of structural morphology, decreased cellulose crystallinity and increased surface area and porosity. These changes in structure reduce the recalcitrance of biomass and makes it susceptible to enzymatic attack.

Recovery of anthocyanins. The anthocyanins are further purified and recovered from the extract by using macroporous resins, membrane separation, or freeze-drying. In the case of resin-assisted separation, the column is packed with macroporous resin that selectively adsorbs the anthocyanins and the separation is based on the principle that the distribution coefficients of anthocyanins in solid and mobile phases are different and hence result in the separation of anthocyanins from impurities. Macroporous resins are known for their fast adsorption rate, large adsorption capacity, low production cost, and easy recyclability.

Conclusion. This study proposes a chemical-free hydrothermal method for the extraction of anthocyanins from purple-stemmed M x giganteus as a non-conventional source. The proposed extraction method involves hydrothermal pretreatment of the biomass at low solid loading (solid: liquid=1:30) at 170° C. for 10 min which led to the recovery of ~94% (w/w) of total anthocyanins in the pretreatment liquor. This chemical-free method of extracting anthocyanins from bioenergy crops would not include any additional unit operation since hydrothermal pretreatment is an integral part of biomass processing to make it suitable for enzymatic saccharification. Under the extraction conditions for maximum recovery of anthocyanins, the enzymatic digestibility of the biomass got enhanced and led to a 2.1-fold increase in the recovery of glucose from the pretreated biomass.

The utilization of bioenergy crops for recovering anthocyanins could be industrially relevant since the productivity of these bioenergy crops is higher than the traditional anthocyanin-rich sources (such as berries, purple tubers, and others). Hence, the overall quantity of pigments recovered (per hectare basis) from these bioenergy crops would be higher than that from conventional sources. However, low solid loading could be one of the major challenges in the scale-up of this process. The solid loading could be increased, and an additional stirring tank could be added before the pretreatment step so that the high loadings of biomass could be completely mixed with the liquid. Further, additional unit operations are required for the purification of anthocyanins from the pretreatment liquor. Overall, the recovery of pigment as a co-product in an integrated biorefinery based on bioenergy crops is expected to improve the economics of the production of biofuels or biochemicals. Hence a detailed techno-economic study is required to evaluate the potential of bioenergy crops for recovering anthocyanins along with the production of biofuels and biochemicals.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Experimental Methods

*M.* x *giganteus* sampling and preparation. Aboveground shoot samples were obtained from three different triploid *M.* x *giganteus* genotypes grown in a field trial at the University of Illinois Energy Farm in Urbana, IL, USA (40.0654 N 88.205 W). The genotypes studied included the predominant commercial cultivar 'Illinois', and two yield-selections from the University of Illinois *miscanthus* breeding program that were also observed to have some purple coloration of their stems. The trial was a randomized complete block design with four replications. Plots consisted of four rows of 12 plants spaced 0.76 m within and between rows. From each plot, 12 shoots were harvested (one per plant from one of the middle two rows) by cutting the stem at ground level. The biomass was dried at 49° C. (up to a final moisture content of 2-3%), shredded, and stored in an air-tight container at −20° C. until further study.

Compositional analysis of *miscanthus* biomass. The composition of three different genotypes of *M.* x *giganteus* whole shoots was determined according to the National Renewable Energy Laboratory's (NREL) analytical protocol—NREL/TP-510-42618. Each biological replicate from the field trial (3 genotypes×4 replications=12 samples in total) was analyzed independently in triplicates. Soxhlet method was used for the extraction of hexane, ethanol, and water-soluble compounds present in the biomass. The extractive-free biomass was hydrolyzed into individual components using two-step acid hydrolysis. Briefly, 300 mg of biomass was incubated in 72% (w/w) sulfuric acid at 30° C. for 60 min. The samples were then diluted using deionized water to bring them down to an acid concentration of 4% (w/w). The diluted samples were then autoclaved at 121° C. for 1 h. All the analyses were performed in triplicate. The acid hydrolysates were vacuum filtered using pre-weighed filtering crucibles that were prepared earlier by heating in a muffle furnace at 575° C. for 4 h. The sugars in the filtered hydrolysate were analyzed using reverse-phase HPLC (RP-HPLC, Waters Corporation, Milford, MA, Alliance system equipped with a 2414 refractive index detector. Separation was achieved using 5 mM sulfuric acid in high purity 18 MΩ deionized water at a flow rate of 0.6 mL/min through a BioRad Aminex 87H (300×7.8 mm, 91 μm particle size) column at 65° C. Concentrations were determined by refractive index versus the mobile phase using Empower software. The acid-soluble lignin (ASL) present in the hydrolysis liquor was determined by measuring the absorbance of the sample at 205 nm on a UV—Visible spectrophotometer. The ASL content was calculated based on the NREL's analytical protocol—NREL/TP-510-42618. The acid-insoluble lignin (AIL) was determined as the weight of the residue left in the crucible dried overnight at 105° C. The ash content was determined by heating the biomass in pre-weighed crucibles in the muffle furnace at 575° C. for 24 h.

Quantification of total anthocyanin concentration. Acidified ethanol was used for complete extraction of anthocyanins from *M.* x *giganteus.* The quantification was done individually for *miscanthus* whole plant, stem, and leaves. The total anthocyanin concentration in *miscanthus* was determined by a previously reported method with slight modifications (Kurambhatti et al., Industrial Crops and Products, 158, 112976, 2020). Briefly, 0.5 g of biomass (0.5 mm size) was mixed with 20 mL of acidified ethanol (ethanol (95% v/v):HCl (1 N), 85:15 v/v) while stirring continuously for 1 h at 30° C. The reaction mixture was filtered using vacuum filtration and the filtrate was analyzed for total anthocyanin concentration. The residue was mixed with acidified ethanol to recover the remaining anthocyanin by stirring it at 30° C. for 2 h. The pH differential method was used for the quantification of the total anthocyanin concentration. Briefly, the anthocyanin extracts were diluted with buffers of pH 1.0 (KCl buffer, 0.25 M) and pH 4.5 (sodium acetate buffer, 0.4 M) followed by measuring their absorbance at 520 and 700 nm using UV/Vis microplate spectrophotometer (Fisherbrand Accuskan Go, Hampton, NH). The monomeric anthocyanin concentration was expressed in terms of cyanidin-3-glucoside (C3G) (Eqn. (1)).

$$\text{Monomeric anthocyanin concentration } (MAC)\left(\frac{\text{mg}}{\text{L}}\right) = \frac{A*D*Mw*1000}{\varepsilon*PL*0.45} \quad \text{Eqn. 1}$$

where, $A=[(A_{520\ nm}-A_{700\ nm})$ at pH 1.0]-[$(A_{520\ nm}-A_{700\ nm})$ at pH 4.5];

$M_W$=449.2 g/mol (for C3G);

ε=26900 L/mol cm (molar extinction coefficient for C3G);

Path Length=1 cm;

D=dilution factor;

0.45 is the conversion factor from established method to microplate method.

Extraction of anthocyanins by hydrothermal pretreatment of *miscanthus.* Hydrothermal pretreatment was used for the recovery of anthocyanins in the pretreatment liquor. *Miscanthus* biomass was loaded in tube reactors at a solid-liquid ratio of 1:30. The pretreatment was carried out in a fluidized sand bath (IFB-51 Industrial Fluidized Bath, Techne Inc., Burlington, NJ, USA). The loaded reactors were immersed in the sand bath and heated to the required temperature. A Thermocouple (Penetration/Immersion Thermocouple Probe Mini Conn, McMaster-Carr, Robbinsville, NJ, USA) connected to a datalogger thermometer, was used to measure the internal temperature of the reactor. The pretreatment was carried out at 130, 150, 170, and 190° C. The desired temperature was maintained for 5, 10, and 15 min. The autohydrolysis reaction was stopped by submerging the reactor vessel in cold water to rapidly decrease the temperature below 50° C. The pretreatment liquor was separated from the pretreated residue by filtration followed by the centrifugation of the liquor at 4000 rpm for 10 min to obtain a clear supernatant. An aliquot of the clear liquor was analyzed for the total anthocyanin concentration by the pH differential method as described in section 2.3. The concentration of sugars and degradation products (such as furfural and 5-HMF) in the liquor was determined using HPLC. The concentration of degradation products increases upon increasing the severity (expressed as $R_o$ in Eqn. (2)) of pretreatment in terms of the temperature and time:

$$Ro = t*\exp\frac{(T-100)}{14.75} \quad \text{Eqn. 2}$$

where, t denotes the time (in min), and T denotes the extraction temperature (in ° C.).

The reference temperature is taken as 100° C. while 14.75 is an empirical factor associated with the temperature and activation energy assuming first-order kinetics. For hydrothermal pretreatment, log $R_o$ is used to study the influence of pretreatment conditions on the composition of biomass. The pretreated residue obtained was enzymatically hydrolyzed to obtain sugars.

Enzymatic digestibility of pretreated *miscanthus* biomass. The enzymatic digestibility of pretreated *miscanthus* biomass was analyzed by following the NREL/TP5100-63351 protocol for enzymatic hydrolysis of lignocellulosic biomass with slight modifications. The pretreated biomass was mixed with citrate buffer (1 M, pH 5.0), 5% (w/v) sodium azide, enzyme solution, and deionized water. The quantity of these components was adjusted according to the moisture content of biomass to achieve a solid loading of 10% (w/v). The enzymatic hydrolysis was performed using NS22257 (Novozymes North America, Inc, Franklinton, NC, USA) at an enzyme dose of 20 mg protein/g of glucan. The reaction mixture was incubated at 50° C. and 150 rpm. Aliquots of the enzymatic reaction mixture were collected at 24, 48, and 72 h. The enzymatic reaction was terminated by submerging the collection vials in boiling water for 60 s followed by centrifugation of sugars was determined using HPLC and the % recovery of glucose was reported after correcting for the glucose content of enzyme blank and substrate blank.

Statistical analysis. T The experimental results have been expressed as average±standard deviation. Two-way analysis of variance (ANOVA) with a general linear model was chosen to determine the best pretreatment conditions for the recovery of anthocyanins from *M.* x *giganteus.* The statistical analysis was done with Minitab Statistical Software version 18 (Pennsylvania State University, USA).

Example 2. Pilot-Scale Processing of *M.* x *giganteus.*

Figure 5:
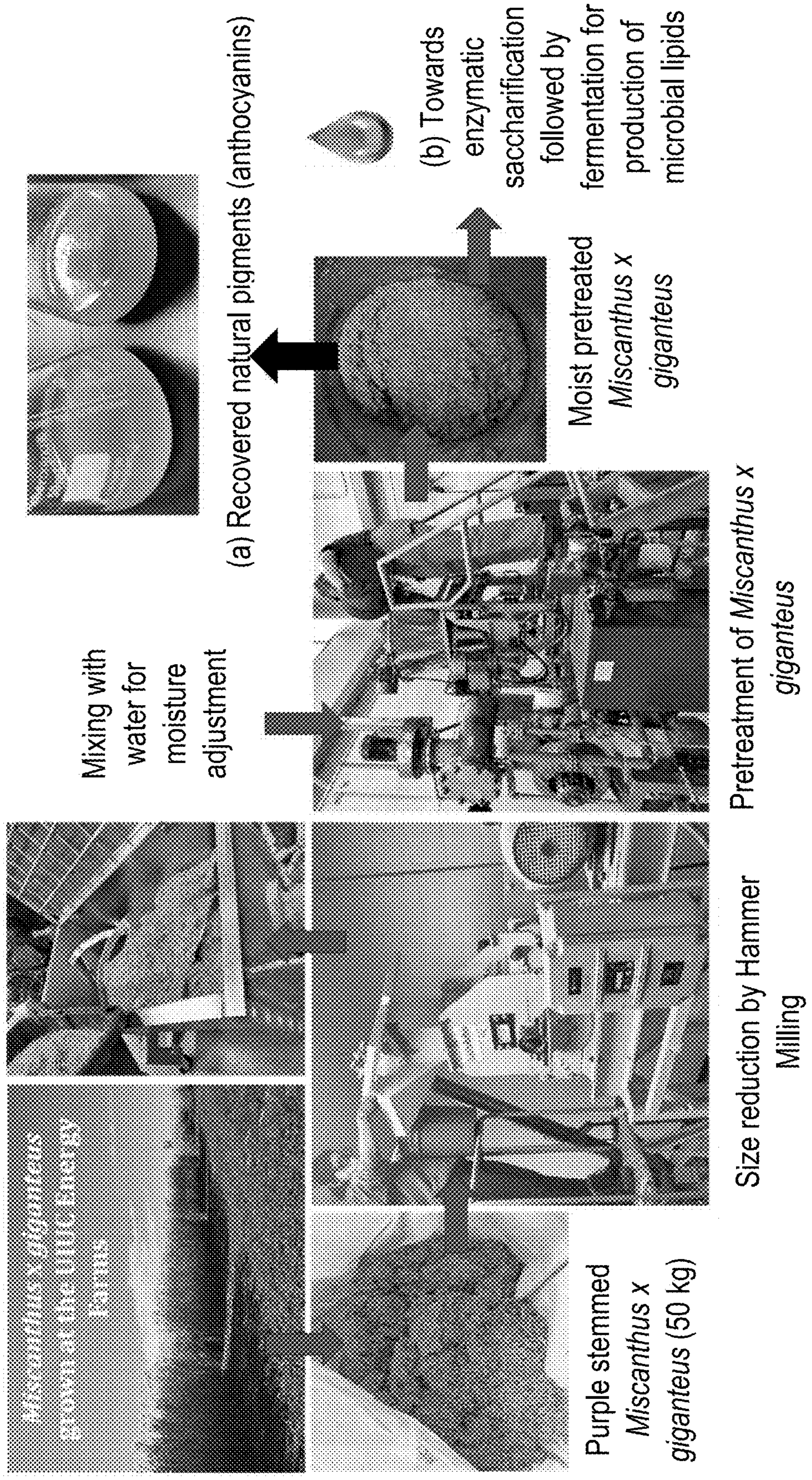
FIG. 5. Demonstration of pilot-scale processing of*M* x *giganteus* 3x '13U1-019-007' for recovery of natural pigments (anthocyanins). Purple stemmed *Miscanthus* x *giganteus* (50 kg): Total Extractives: 11.8±1.9%; Total Glucan: 41.3±1.8%; Total Xylan: 21.2±2.6%; Total Ash: 2.1±0.4%; Acid Insoluble Lignin: 19.1±0.1%; Acid Soluble Lignin: 1.1±0.1%. Moist pretreated *Miscanthus* x *giganteus*: Total Extractives: 31.5±0.4%; Total Glucan: 35.1±2.3%; Total Xylan: 15.6±1.1%; Total Ash: 1.92±0.01%; Acid Insoluble Lignin: 18.7±0.5%; Acid Soluble Lignin: 1.2±0.1%.
Figure 6:
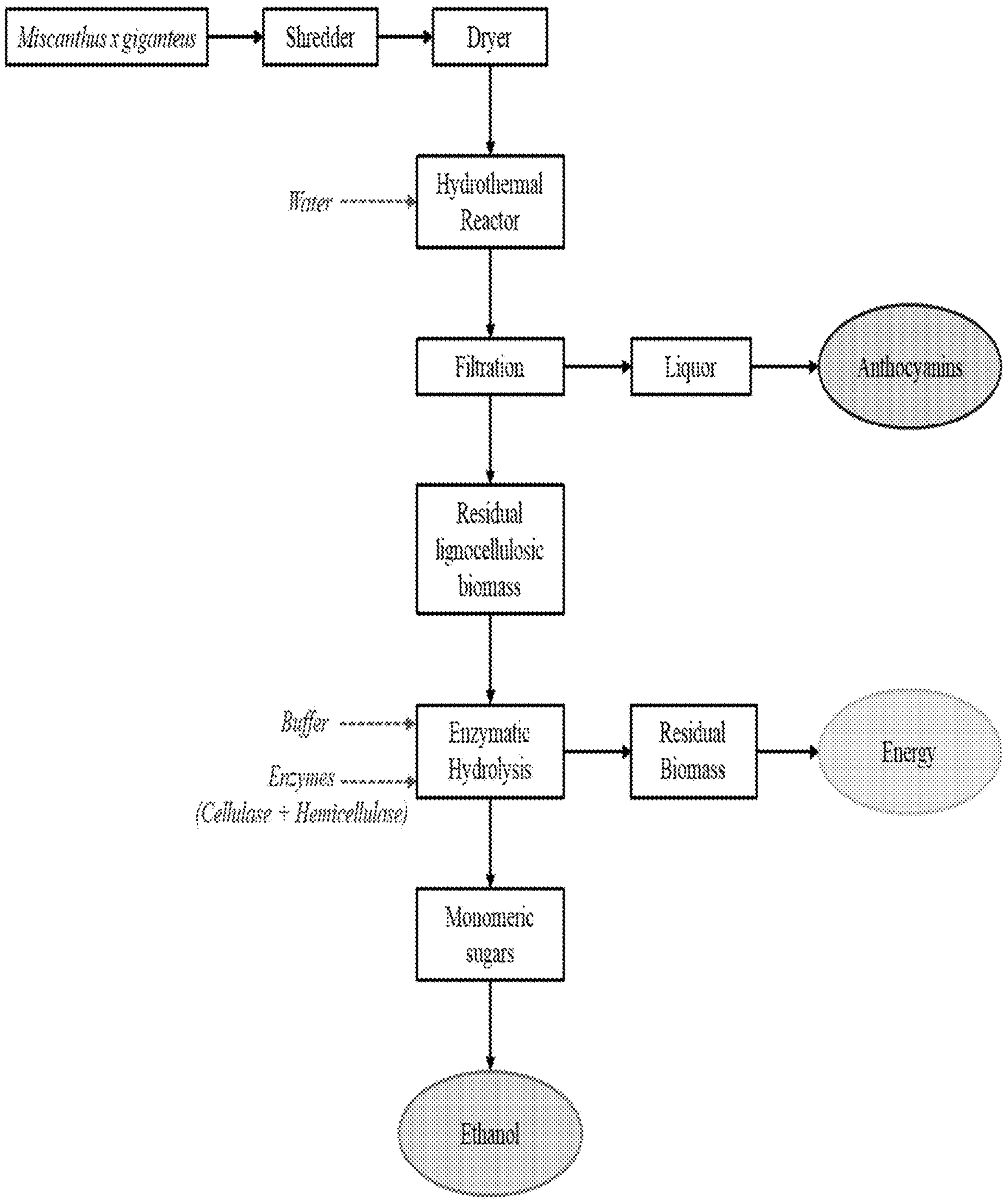
FIG. 6. Process design for extraction of anthocyanin from *Miscanthus* x *giganteus* as a co-product in an ethanol biorefinery.

Above ground shoot samples of *Miscanthus* x *giganteus* were harvested in bulk quantities (~50 kg) from the University of Illinois Energy Farm in Urbana, Illinois in December 2022. The dried biomass was shredded while harvesting and the particle size was further reduced by grinding it using a hammer mill (W-8-H, Schutte-Buffalo Hammermill, Buffalo, NY) equipped with a 3 mm sieve. The moisture content of the biomass was adjusted to 50% (dry weight basis). The hydrothermal pretreatment was carried out using the pilot-scale continuous reactor (SüPR•2G Reactors, AdvanceBio system LLC., Milford, OH) at 170° C. The moist biomass was then screw-fed into the reactor and pretreated at 170° C. for 10 min. The reaction temperature was controlled by the pressure of the injected steam while the residence time was controlled by setting the feeding rate of the auger within the reactor. Around 70% (w/w) of the total anthocyanins were recovered from the moist pretreated biomass obtained after pilot scale processing. However, the pilot-scale continuous pretreatment reactor does not produce hydrolysis liquor and hence an additional unit operation was required to extract the natural colorants from the pretreatment liquor FIG. 5 and FIG. 6).

Key Points:

- *Miscanthus* x *giganteus* has been evaluated as a source of anthocyanin pigments.
- Hydrothermal pretreatment resulted in a chemical-free recovery of anthocyanins.
- The pretreated residue exhibits enhanced enzymatic digestibility.

Hydrothermal pretreatment increases the enzymatic digestibility of cellulose-enriched residue. Enzymatic hydrolysis has been used to valorize the pretreated residue into sugar monomers. The biomass pretreated at 170° C. for 10 min showed the highest anthocyanin concentration in the liquor and the residue was used for enzymatic hydrolysis. The amount of glucose released over time upon enzymatic hydrolysis is as shown in FIG. 4. The % recovery of glucose upon enzymatic saccharification increased from 58.6±2.8% at 24 h to 70.6±0.5% after 72 h. However, for untreated *miscanthus* biomass, only 33.3±1.4% of glucose was released after 72 h. The glucose recovery increased with time and the pretreatment led to a 2.1-fold increase in the overall recovery of glucose from the pretreated biomass at the end of 72 h. The improved enzymatic digestibility of biomass upon hydrothermal pretreatment could be attributed to the disruption of structural morphology, decreased cellulose crystallinity, and increased surface area and porosity. These changes in structure reduce the recalcitrance of biomass and make it susceptible to enzymatic attack.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the claims that follow.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition of an extract from biomass based on the dry weight of the biomass, the composition comprising about 15-65 μg anthocyanin/g dry biomass, about 1.6-2.1 g glucose/100 g dry biomass, about 1.5-1.9 g xylose/100 g dry biomass, about 0.3-0.8 g arabinose/100 g dry biomass, about 0.03-0.2 g lactic acid/100 g dry biomass, about 0.1-0.3 g acetic acid/100 g dry biomass, about 0-0.03 g furfural/100 g dry biomass, and 0-0.03 g 5-hydroxymethylfurfural/100 g dry biomass.

2. The composition of claim 1 comprising 38.7±26.9 μg anthocyanin/g dry biomass, 1.85±0.07 g glucose/100 g dry biomass, 1.51±0.04 g xylose/100 g dry biomass, 0.76±0.04 g arabinose/100 g dry biomass, 0.17±0.01 g lactic acid/100 g dry biomass, 0.18±0.00 g acetic acid/100 g dry biomass, 0 to 0.01 g furfural/100 g dry biomass, and 0 to 0.01 g 5-hydroxymethylfurfural/100 g dry biomass.

3. A composition comprising, based on a dry weight of an above-ground whole shoot of *Miscanthus* x *giganteus*, about 15-65 μg anthocyanin/g *Miscanthus* x *giganteus*, glucose, xylose, arabinose, lactic acid, and acetic acid, and optionally furfural, 5-hydroxymethylfurfural, or both, wherein, if present, the composition comprises less than 0.01 g furfural/100 g *M.* x *giganteus*, and if present, the composition comprises less than 0.01 g 5-hydroxymethylfurfural/100 g *M.* x *giganteus*, wherein the composition is prepared by a hydrothermal process comprising:

a) drying and shredding a crop of *M.* x *giganteus;* b) heating a mixture of the crop and water under pressure at a temperature of about 130° C. to about 190° C. for a heating time of about 5 minutes to about 15 minutes to form a heated mixture, wherein the pressure is about 6 atmospheres to about 12 atmospheres;

c) cooling the heated mixture at a cooling rate of about 2° C./minute to about 20° C./minute until the heated mixture is at a temperature below about 50° C.; and d) isolating a water extract comprising the composition.

4. The composition of claim 3 wherein the water extract comprises no detectable amount of furfural/100 g *M.* x *giganteus* and no detectable amount of 5-hydroxymethylfurfural/100 g *M.* x *giganteus* as determined by high performance liquid chromatography.

5. The composition of claim 4 wherein the water extract comprises 38.7±26.9 μg anthocyanin/g *M.* x *giganteus*, 1.85±0.07 g glucose/100 g *M.* x *giganteus,* 1.51 ±0.04 g xylose/100 g *M.* x *giganteus,* 0.76±0.04 g arabinose/100 g *M.* x *giganteus,* 0.17±0.01 g lactic acid/100 g *M.* x *giganteus*, and 0.18±0.00 g acetic acid/100 g *M.* x *giganteus.*

* * * * *